(12) United States Patent
Gedouin et al.

(10) Patent No.: US 6,207,438 B1
(45) Date of Patent: Mar. 27, 2001

(54) METHOD FOR PREPARING A PRODUCT IN PARTICULAR FOR PREVENTING AND CURING SKIN DISEASES, AND RESULTING PRODUCT

(75) Inventors: Jean Gedouin; Romuald Vallee, both of Saint-Malo (FR)

(73) Assignee: Codif International SA, Saint-Malo, Cedex (FR)

( * ) Notice: Subject to any disclaimer, the term of this patent is extended or adjusted under 35 U.S.C. 154(b) by 0 days.

(21) Appl. No.: 09/068,254

(22) PCT Filed: Sep. 26, 1997

(86) PCT No.: PCT/FR97/01705

§ 371 Date: May 5, 1998

§ 102(e) Date: May 5, 1998

(87) PCT Pub. No.: WO98/13049

PCT Pub. Date: Apr. 2, 1998

(51) Int. Cl.$^7$ .................................................. C12N 9/88

(52) U.S. Cl. ..................... 435/232; 424/195.1; 435/136; 435/137; 435/257.1; 435/257.3

(58) Field of Search ..................... 424/195.1; 435/136, 435/137, 257.1, 72, 257.3, 232

Primary Examiner—Leon B. Lankford, Jr.
(74) Attorney, Agent, or Firm—Laff, Whitesel & Saret, Ltd.; J. Warren Whitesel

(57) ABSTRACT

The invention relates to a process for the preparation of a product and to the product itself to prevent and care for skin disorders. The process includes using a natural sodium alginate extract, and the submission of this extract to at least on depolymerization treatment. The resulting product includes oligo-alginate chains and uronic acids. The product is used to treat cutaneous rashes, allergic reactions to cosmetic compositions, and the cutaneous effects of aging.

15 Claims, No Drawings

METHOD FOR PREPARING A PRODUCT IN PARTICULAR FOR PREVENTING AND CURING SKIN DISEASES, AND RESULTING PRODUCT

The invention relates to a process for the preparation of a product intended in particular to prevent and cure disorders of the skin, such as cutaneous rashes or allergic reactions to cosmetic compositions, and a product of this nature. The invention likewise relates to a product intended to combat the effects of ageing on the skin, whether natural, due to pollution, or resulting from exposure to ultraviolet radiation.

The work by Susuma Tonegawa, Nobel Prizewinner for Medicine in 1987, has demonstrated the immunological function of certain epidermic cells, the Langerhans' cells, in relation to attacks located in the epidermis of the skin. The Langerhans' cells, which belong to a family of cells known as the lymphoid dendrites, are essentially located in the central layers of the epidermis. Despite their low density, they play a part in determining information and monitoring the whole of the epidermis, thanks to their dendritic nature and their migratory capacity in particular.

The Langerhans' cells are capable both of exerting a phagocyte effect on foreign bodies or on allergens which penetrate the epidermis, and of transmitting antigens to specific immuno-capable cells, referred to as T cells. The activation and protection of the Langerhans' cells accordingly allows for the intrinsic defence processes of the epidermis to be stimulated.

It is known that these cells are directly exposed to the ultraviolet radiation resulting from exposure to the sun. Recent studies have shown that this radiation incurs, to a greater or lesser degree, a reduction on the one hand in the membrane markers, and therefore a change in the capacity for the presentation of antigens by the immune-capable cells, and, on the other, the disappearance of the dendrites which characterise the Langerhans' cells. In the event of prolonged exposure to the sun, the ultraviolet radiation will inhibit the Langerhans' cells, and their number will decrease.

Attempts have been made to create products which are capable of protecting and activating the Langerhans' cells against the ultraviolet radiation which is frequently encountered by the epidermis.

Accordingly, such products are known which are prepared on the basis of yeast extracts, and which are constituted from polysaccharides of vegetable origin. The products may be cited, for example, which belong to the family of the β-1,3 glucanes, recognised by the membrane receptors of the Langerhans' cells, and which allow the said cells to maintain, to a certain degree, their macrophage activity and to protect the immuno-capable cells of the epidermis.

One major disadvantage of these products referred to lies in their often insufficient penetration into the epidermis, which is due to the substantial size of the polysaccharide molecules of which the said products consist.

The objective of the invention is to provide a process for the creation of a product which is particularly intended to prevent and cure disorders of the skin, and such a product, such that the said product can penetrate in a satisfactory manner into the epidermis, and thus present satisfactory protective activity for the skin in relation to external attack.

To this end, a process for the creation of such a product is one that consists of using a natural extract of sodium alginate, and to submit the said extract to at least one depolymerisation treatment.

According to another characteristic of the invention, the said extract is submitted to an enzymatic depolymerisation treatment by means of a lyase alginate.

For preference, and following the said enzymatic treatment, the said depolymerised extract is submitted to hydrolysis in an acid environment.

A product according to the invention, intended to prevent and cure disorders of the skin, is one such as comprises chains of oligo-alginates and uronic acids.

For preference, it also comprises at least one oligoelement, in cationic form, forming a chelate with the said chains.

The said chelate comprises for example $Zn^{+2}$ ions, or a grouping of $Mn^{2+}$ and $Mg^{2+}$ ions.

According to a variant embodiment of the invention, the said product also comprises natural extracts of algae of the *chlorella* type.

A product according to the invention is intended to protect the Langerhans' cells in the epidermis against ultraviolet radiation.

It is likewise intended to increase the epidermic concentration of the interleukin 1α.

A product according to the invention of the type containing the said chelate is intended to provide an anti-radical effect in respect of the free radicals produced by the ultraviolet radiation.

more precisely, the said product is thus intended to protect the cells of the dermis against the oxidation of proteins, and the fragmentation of the DNA.

The said product, comprising the said chelate, is likewise intended to provide an inhibitor effect in respect of the activity of the reductase enzyme 5α.

The said product comprising the said chelate is likewise intended to provide an inhibitor effect in respect of the pathogenic bacterial strain *Propionibacterium acnes*.

The characteristics of the invention referred tom as well as others, will become clearer by reading the following description of several embodiments.

According to a first embodiment of the invention, a product according to the invention consists of oligosaccharides of the type comprising, on the one hand, oligoalginates, and, on the other, acids which feature a structure analogous to that of the alpha-hydroxyl acids, such as the uronic acids.

The said product is prepared on the one hand from an algae extract, for preference of the species *Laminaria digitata*, which are based on polysaccharides constituted from a sodium alginate. A process for the preparation of the said product is the following.

The said extract of sodium alginate is first submitted to an enzymatic depolymerisation process. Use is made for this purpose of an enzyme of the lyase mannuronate type, and for preference a lyase alginate. This enzyme, obtained by bacterial fermentation, allows for depolymerisation by β-elimination of the alternate blocks of the sodium alginate molecule, which consist of chains of α-L-sodium gluronate and β-D-sodium mannuronate, linked in 1, 4. In addition to this, the aforesaid enzyme allows for the viscosity of the solution of sodium alginate to be reduced very rapidly at the end of the depolymerisation stage.

For preference, the depolymerised alginate extract is then subjected to partial hydrolysis in an acid medium, in such a way as to obtain a product characterised by a degree of polymerisation which is again reduced in relation to that of the said depolymerised extract.

It will be noted that this hydrolysis is greatly facilitated by the implementation of the first stage, due to the reduced viscosity of the alginate extract by the said enzyme, and thanks to the prior depolymerisation of the said blocks characterising the sodium alginate.

In addition to this, it is to be noted that the said enzyme allows for the gelification of the alginic acid to be limited, following acidification, which allows for a good level of activity to be conferred on the product obtained.

Purely by way of indication, two examples of the preparation of the product according to the invention are given hereinafter.

EXAMPLE 1

The algae extract constituted from sodium alginate is first solutized for one hour at a concentration of 5%.

The solutized alginate extract is then subjected to enzymatic depolymerisation at a temperature of 25° C., for four hours, by means of a lyase alginate designated AL 951. In addition to this, the enzyme/alginate mass ratio is 0.01%, and the mean pH is 7.5.

The mean molecular weights in terms of numbers of the said solutized extract are determined during and after the said enzymatic depolymerisation, by the method known as "addition of double conjugated bonds" (see Appendix I).

From this can be deduced the mean degree of polymerisation in terms of numbers of the said extract at the two aforesaid times.

In this embodiment, the said degree of polymerisation of the extract of alginate is 96, following the enzymatic treatment.

This alginate extract, of a degree of polymerisation equal to 96 can constitute a product according to the invention which is intended to exert an effect on the skin, and essentially on the skin surface.

For preference, the depolymerised extract is then partially hydrolysed in an acid medium, the hydrolysis being carried out over four hours at a pH of 1.5 and at 94° C. For this purpose, sulphuric acid is added to the said extract, the ratio of acid to alginate being 30% at dry weight. This reaction is stopped by cooling until the temperature of the medium reaches 20° C., which is the case after one hour.

The mean molecular weight is then determined, as a number, of the hydrolysed extract by the SOMOGYI-NELSON method, referred to as the "reducer sugars dosage" (see Appendix II), and the mean degree of polymerisation is deduced in terms of a number from the product which is finally obtained.

In this embodiment, the said degree of polymerisation of the product according to the invention is 12.

EXAMPLE 2

In the same manner as described previously, the sodium alginate extract is first solutized for one hour at a concentration of 5%.

The solutized extract is then submitted to enzymatic depolymerisation at a temperature of 25° C., for twenty three hours, by means of the said lyase alginate. In addition to this, the weight ratio of enzyme to alginate is 0.1% and the pH of the medium is maintained at 7.5.

Following the enzymatic treatment, the mean degree of polymerisation as a number is determined as indicated in Example 1.

In this embodiment, the said degree of polymerisation of the extract treated by the lyase alginate is 9.

The said treated extract is then submitted to acid hydrolysis under the same conditions as the previous example, and the degree of polymerisation in terms of a number is then determined in the same manner for the product finally obtained.

In this embodiment, the product according to the invention is characterised by a degree of polymerisation equal to 4.

It will be noted that the reduced degrees of polymerisation which have finally been obtained in the said embodiments favour the cutaneous penetration of the product according to the invention, and with regard to its action in depth in the stratum corneum in particular.

It will also be noted that the hydrolysis in the acid medium constitutes an optional stage of the process according to the invention. It would in fact be sufficient to proceed with the single enzymatic depolymerisation, from the moment at which the degree of polymerisation of the product obtained following the lyase alginate treatment would be such that the penetration of the said product into the skin would be sufficient. By way of indication, the maximum admissible degree of polymerisation of the product according to the invention is about 20 in order to produce the said action in the depth indicated.

It will also be noted that the product according to this first embodiment of the invention features stability within a satisfactory period of time, according to the chromatographic tests to which it has been subjected.

In order to attest the immuno-modulating effect on the epidermis of a product according to the invention, a number of experiments were conducted, after submitting skin samples to irradiation under ultraviolet rays of class B (U, V, B), which consisted of displaying and counting the Langerhans' cells present in the epidermis, with the aid of a fluorescent microscope.

Set out hereinafter in a summary detailing the method of procedure and the results relating to these experiments, these being for three different products corresponding to the first embodiment of the invention.

Each of the said products is characterised by the same volumetric fraction of oligosaccharides equal to 0.25%, and the pH of these said products is 2, 4, and 7 respectively. These products will be designated respectively as ALGpH2, ALGpH4, and ALGpH7 in the remainder of the description.

Samples of skin from a healthy subject, obtained following abdominal surgical intervention, are placed live in an appropriate culture medium. Four series of samples are prepared:

The first series (control) is such that each sample contained does not receive the product according to the invention and is not subject to UVB irradiation;

The second series (irradiated control) is such that each extract contained does not receive the product according to the invention, but is subjected to UVB irradiation;

The third series (treated and not irradiated) is such that each sample receives the product according to the invention, but is not subject to UVB irradiation;

The fourth series (treated and irradiated) is such that each sample receives the product according to the invention, and is subjected to UVB irradiation.

The four series of samples are frozen by immersion in isopentane, cooled to −55° C. in liquid nitrogen.

A number of frontal cuts are then effected inside a cryostat at a temperature of −16° C., the effect of which is to stop the immunising activity of the Langerhans' cells.

A first antibody and a second antibody are then incubated in each sample, these antibodies then making it possible, by the immunofluorescence technique, to display the activity of the Langerhans' cells. In fact, the Langerhans' cells are only active if they are playing their antigen role by blocking the antibodies, the said antigenic action being capable of observation under the fluorescence microscope.

The first antibody is capable of recognising the Langerhans' cells and the second antibody, coupled to fluorescent molecules of tetramethyl-rhodamine-isothiocyanate (TRITC), is capable of colouring the said cells.

The cut and incubated samples are observed under the fluorescence microscope, in order to be able to display and enumerate the Langerhans' cells characterising each sample.

The samples were photographed and studied for each series of samples, in such as way as to be able to evaluate the mean number of Langerhans' cells per unit of length of the epidermis for the whole of the samples observed. Likewise, the standard error mean (SEM) was determined for each series studied, which is obtained by dividing the typical deviation measured by the square root of the number of samples of the series concerned. In view of the fact that the total number of samples were substantial, two categories of measurements were carried out, the first being intended to determine the immuno-modulative effect of the products ALGpH2 and ALGpH7, while the second category was intended to determine the immuno-modulative effect of the third product ALGpH4 according to the invention.

The immuno-modulative effect of each product has been enumerated by means of the following formula:

$$I.E. (\%) = \frac{\Delta N(\text{control} - \text{irradiated control}) - \Delta N(\text{treated} - \text{treated irradiated})}{\Delta N(\text{control} - \text{irradiated control})} \times 100$$

where

I.E. represents the value as a percentage of the said immuno-modulative effect;

$\Delta N$ (control-irradiated control) represents the number of Langerhans' cells of the "control" series, less that of the "irradiated control" series, and;

$\Delta N$ (treated-treated irradiated) represents the number of Langerhans' cells of the "treated" series, less that of the "treated irradiated" series.

The value found for I.E. allows for a definition in a qualitative and standardised manner of the immuno-modulative effect of the product tested. In particular:

If $70\% < I.E. < 100\%$, then the product has a very good immuno-modulative effect;

If $I.E. > 100\%$, then the product has an absolute immuno-modulative effect.

Tables I and II below demonstrate these measurements.

TABLE I

| Series of samples | Mean number of Langerhans' cells per cm of epidermis ± SEM | Variation and rate of variation of number of Langerhans' cells per cm of epidermis after radiation | Immuno-modulation effect |
|---|---|---|---|
| Control | 305 ± 22 | | |
| Irradiated control | 85 ± 13 | −220 cells −72.1% | |
| Treated with ALGpH2 and not irradiated | 276 ± 55 | +113 cells +40.9% | 151.4% |
| Treated with ALGpH2 and irradiated | 389 ± 56 | | |
| Treated with ALGpH7 and not irradiated | 262 ± 23 | −8 cells −3.1% | 96% |

TABLE I-continued

| Series of samples | Mean number of Langerhans' cells per cm of epidermis ± SEM | Variation and rate of variation of number of Langerhans' cells per cm of epidermis after radiation | Immuno-modulation effect |
|---|---|---|---|
| Treated with ALGpH7 and irradiated | 254 ± 31 | | |

TABLE II

| Series of samples | Mean number of Langerhans' cells per cm of epidermis ± SEM | Variation and rate of variation of number of Langerhans' cells per cm of epidermis after radiation | Immuno-modulation effect |
|---|---|---|---|
| Control | 151 ± 14 | | |
| Irradiated control | 58 ± 7 | −93 cells 61.6% | |
| Treated with ALGpH4 and not irradiated | 303 ± 18 | | |
| Treated with ALGpH4 and irradiated | 326 ± 20 | +23 cells +7.6% | 124.7% |

It appears after reading Tables I and II that the ALGpH2 and ALGpH4 products according to the invention have an absolute immuno-modulating effect, in other words, they provide total protection for the Langerhans' cells contained in the epidermis, following its irradiation under ultraviolet rays.

It likewise appears that the product according to the invention ALGpH7 has a very substantial immuno-modulating effect, of such a nature as to enable it to obtain an almost total protection of the Langerhans' cells in respect of ultraviolet rays.

As a result, the macrophage activity of the said cells is preserved thanks to the product according to the invention, and the protection of the epidermis in respect of external attack is improved.

In a second experiment, the effect of the ALGpH4 in several doses was confirmed. UVB irradiation incurred a reduction of 70% in the number of Langerhans' cells per cm of epidermis.

Following the treatment of the skin samples by the products according to the invention, corresponding respectively to the volumetric fractions of the oligosaccharides ALGpH4 tested, of 0.5%, 2%, and 3.5%, immunoprotector effects were obtained of 35%, 64%, and 75% (effect-dose ratio).

An evaluation was also made of the phototoxic potential in vivo of the said products according to a first embodiment of the invention. To do this, ten subjects were selected, aged between 31 and 64, not presenting any cutaneous conditions or any medical case history likely to argue against the topical application of the substances.

An adhesive occlusive bandage containing about 0.2 ml of the product according to the invention was applied to them on one arm, for 24 hours, and the arm bearing the bandage was then subjected to UVA irradiation.

It was discovered that the said product did not induce a phototoxic reaction of the erythemic or oedemic type.

Likewise, two in vivo tests were conducted, which are generally applied in order to allow for the determination of the possible mollifying effect of a product.

The first test is known as the epidermic interleukin 1α dosage rate, after topical treatment. This consists of the following operations:

On the first day ($J_0$), volunteers (10 healthy volunteers aged 17 on average in this example) were selected.

A product according to the said first embodiment was applied to the forearm (in the ratio of 2 μl/cm2) at $t_0$ (initially) and $t_{12}$ (12 hours later). The next day (J1), the interleukin 1α was assessed on a treated area (ZT) and on an untreated area (ZNT). The rate of the interleukin 1α was metered by the ELISA technique, using a specific monoclonal antibody of interleukin 1α and a second antibody conjugate to the peroxidase. At the end of the substrate-peroxidase reaction, the dosage was read off with the aid of a microplate spectrophotometer reader.

In theory, it is known that the stronger the optical density measured, the greater the concentration of interleukin 1α. An increase in the concentration of the epidermic interleukin 1α translates into a mollifying effect of the product.

The rate values of the interleukin 1α, and the typical deviation from the mean (SEM) obtained from ten volunteers, were calculated for the corresponding area treated and the area untreated.

The variation from the mean values (Δ%) were expressed by applying the following formula:

$$\Delta\% = (ZT-ZNT)/ZNT \times 100$$

The data from the two treatments (the control area and the treated area) were analyzed by a Student test on the apparent data. The results are presented in the table below:

|  | Control area, not treated | Area treated by oligoalginate of DP = 10 at 5% (v/v) |
|---|---|---|
| Rate in pg/ml of mean interleukin 1α ±SEM (n = 10 persons) | 84 ± 10 | 93 ± 9 |
| Δ (treated-control) |  | 11.1% |
| Error probability |  | 0.02% |

This test showed that, after two standard applications on the forearms, spaced at 12 hour intervals, the said product at 5% significantly increases the rate of epidermic interleukin 1α (Δ%=+11.1%). It will also be noted that the error probability of this test is less than 0.05, which allows the said test to be validated.

Under these experimental conditions, the said product according to the invention may be considered as a mollifying product.

The second test is known as the Stinging Test.

This is a "lactic acid anti-stinging test", applied to eight volunteers after 28 days of twice-daily use of products according to the invention, characterised by a volumetric fraction of 5% in a cosmetic base.

This test initially allows for an evaluation of the cutaneous reactivity of the volunteers included in the study, then, secondly, for an evaluation of the anti-sting effect of the product tested.

On the first day ($J_0$), a stinging test was carried out in order to evaluate the reactivity of the skin in the area of the face. The product was distributed among the eight volunteers retained, who applied the said product morning and evening for the said 28 days.

In conformity with this test, each volunteer carried out an application on the nasal line of a solution of 10% lactic acid on one side, and distilled water on the other.

10 seconds, 2.5 minutes, and 5 minutes after the application, the sensations of the volunteers were evaluated according to the following scale:

0: No stinging
1: Slight sensation
2: Moderate sensation
3: Severe sensation

An overall reactivity score which takes account of the three items of data indicated above has been calculated in accordance with the formula:

Overall score=Total scores (lactic acid)−total scores (distilled water).

After these 28 days ($J_{28}$), a new stinging test was carried out in the same manner, with the same reactivity score calculations.

The results are shown in the table below.

Reactivity scores obtained before and after 28 days of treatment (individual values):

| Volunteer | $J_0$ | $J_{28}$ | $J_{28} - J_0$ |
|---|---|---|---|
| 1 | 4 | 2 | −2 |
| 2 | 3 | 2 | −1 |
| 3 | 5 | 4 | −1 |
| 4 | 4 | 1 | −3 |
| 5 | 3 | 3 | 0 |
| 6 | 4 | 3 | −1 |
| 7 | 6 | 5 | −1 |
| 8 | 4 | 1 | −3 |
| Mean | 4.1 | 2.6 | −1.5 |

The greater the differential between $J_0$ and $J_{28}$ (with $J_0 < J_{28}$), the more the reactivity threshold is reduced.

The mean reactivity scores obtained for all the volunteers were 4.1 on $J_0$ and 2.6 on $J_{28}$, being a reduction of 36.6%.

Under the conditions of the trial, a daily application of the said product according to the invention included at 1.5% in a cosmetic base had the effect of reducing the reactivity of the skin. An anti-sting effect of the product was accordingly demonstrated.

According to a second embodiment of the invention, a product according to the invention is obtained by adding to a product according to the first embodiment (for preference of a degree of polymerisation on 10), a solution comprising one or more oligo-elements provided in order to create a stable complex, also referred to as a chelate, with the said product. The said oligo-elements are comprised of mineral elements in cationic form.

By way purely of indication, described hereinafter are two examples of the preparation of chelates comprising products according to the invention.

EXAMPLE 1

Extracts of oligoalginates of the type referred to above in the said first mode are resolutized at 30° C. (pH=4.13). Then, at a temperature of 20° C., the pH value of the said extracts is readjusted to 5.60 with sodium hydroxide 1N. After centrifuging for 20 minutes at 8000 rev/min, 100 grams of the resultant fraction is mixed to a solution containing minerals comprising zinc ions.

By way of example, 8 ml of ultra pure water is used, containing 0.5789 g of zinc sulphate ($Zn\ SO_4, H_2O$) for the creation of the said chelate.

EXAMPLE 2

In this example, the said stages of resolutization, readjustment of the pH factor, and the centrifuging are identical. The only difference is the mineral which is added.

This solution comprises a mixture of magnesium and manganese ions, in the following proportions:

Ultra pure water is used, containing 2.652 g of magnesium sulphate ($MgSO_4$, $7H_2O$)+10 ml of ultra pure water containing 1.807 g manganese sulphate ($MnSO_4$, $H_2O$) for the creation of the said chelate.

The mixture obtained is stirred for one hour at ambient temperature, then centrifuged for 20 minutes at 8000 rev/min.

The fraction derived containing the chelate is then kept at ambient temperature.

Details are provided hereinafter of the additional actions which provide a chelate according to the first preparation example (oligosaccharide-zinc chelate), as well as the effects referred to earlier obtained for a product according to the said first embodiment. Two in vitro tests have established an anti-acne effect for this chelate.

First In Vitro Test Establishing an Inhibitor Effect of the Said Chelate on the Enzyme 5α Reductase It is known that enzymes of the type 5α reductase (5αR) transform testosterone into 17β-hydrosy-5α-androstan-3-one or 5-dehydrotestosterone (5HDT). This reaction is crucial in the action of androgens. These enzymes are present in the keratinocytes of the epidermis, in the fibroblasts of the dermis, and in the sebaccous glands in particular.

The inhibitor effect of the chelate oligosaccharide-Zn has been evaluated by a radio-chemical method, on the activity of 5αR of an extract of mammal prostate, such as that of the dog. In this experiment, in the presence of NADPH (nicotinamide adenine dinucleotide phosphate) and a system of regeneration of the NADPH, the following reactions were essentially obtained:

| Testosterone -> 5α-dihydrotestosterone -> 5α-androtanediols* | | | | |
|---|---|---|---|---|
| T | 5αR | 5DHT | 3HSD** | ASD | where *= isomers 3β, 17β-diol and 3α, 17β-diol
and **= 3-hydroxysteroid dehydrogenases.

Material and Method

Solutions of the product were created at five times the final concentration used in the reaction, in a citrate-phosphate buffer at 0.1 M and pH=5.6 (buffer used in the 5αR reaction). The 5αR reference inhibitor was finasteride (Chibro-Prosacar®, in 5 mg tablets), and tested at the concentration of 500 µg/ml after dilution in the citrate-phosphate buffer at 0.1 M.

The enzymatic extract used was a raw extract of dog prostate prepared in a tris buffer of 0.1 M/sucrose 20%, pH=7.5. The sample was calibrated in such a way as to transform approximately 0.1 pmole of testosterone with 50 µl of extract (being an arbitrary unit of the enzyme).

The mixtures were incubated for 4 hours at 37° C., then the testosterone and the derivatives formed were extracted by 500 µl of dichloromethane. The fraction of dichloromethane was drawn off, dried under a nitrogen flow, and chromatographed on silica in a dichloromethane/ethyl acetate/methanol system (proportions 85:15:3). The plates obtained were autoradiographed on Kodak MP® films.

The evaluation of the quantity of testosterone transformed was carried out after sectioning the products formed and counting them in liquid scintillation.

The effect of the finasteride and the oligo-saccharide-Zn chelate on the transformation of the testosterone into DHT and ASD is illustrated in the table below.

(T=controls without enzyme; E=controls plus enzyme; F=finasteride; P1=oligosaccharide at 5%; P2=oligosaccharides at 1%):

| No. | Product | Conc (%) | cpm DHT | cpm ASD | cpm total | Mean | Mean e − T | 5αR activity | % inhibition |
|---|---|---|---|---|---|---|---|---|---|
| T | — | — | 226 | 159 | 385 | 433 | 0 | 0 | |
| T | — | — | 330 | 153 | 483 | | | | |
| T | — | — | 264 | 167 | 431 | | | | |
| E | — | — | 939 | 3923 | 4862 | 4769 | 4336 | 100 | 0 |
| E | — | — | 779 | 4008 | 4787 | | | | |
| E | — | — | 929 | 3730 | 4659 | | | | |
| F | finast- | 0.1 mM | 343 | 880 | 1223 | 1080 | 647 | 15 | 85 |
| F | eride | 0.1 mM | 262 | 748 | 1010 | | | | |
| F | | 01 mM | 359 | 647 | 1006 | | | | |
| P1 | finast- | 5 (%)626 | 2812 | 3400 | 3629 | 3196 | 74 | 26 | |
| P1 | eride | 5 (%)555 | 3235 | 3790 | | | | | |
| P2 | oligosac- | 1 (%)786 | 3652 | 4438 | 4512 | 4079 | 94 | 6 | |
| P2 | charide- | 1 (%)842 | 3732 | 4574 | | | | | |
| P2 | Zn chelate | 1 (%)801 | 3724 | 4525 | | | | | |

Results

The finasteride inhibits 85% of the transformation of testosterone into 5DHT and ASD.

The oligosaccharide-Zn chelate, tested at 1% (v/v) did not have any overall inhibitor effect. At 5%, it inhibited 26% of the activity of the 5α reductase.

Conclusion

This oligosaccharide-Zn chelate at 5% (v/v) features an interesting inhibitor effect on the activity of the 5α reductase, from which it derives its interesting effect against acne.

Second In Vitro Test Establishing an Effect on Pathogenic and Non-pathogenic Flora The effects of an oligosaccharide of a degree of polymerisation close to 10 according to the said first method, and of a chelate of this oligosaccharide+Zn, were evaluated on the non-pathogenic strain *Micrococcus kristinae,* the pathogenic strain *Staphylococcus aureus,* and the pathogenic strain *Propionibacterium acnes*. This latter strain is particularly involved in the irritations occurring in the course of cutaneous acne infections.

Material and Method

The bacteria are cultured in a saline medium (5.6 g/l of NaCl 2.812 g/l of $KH_2PO_4$), containing pancreatic peptone (5.625 g/l) and extracts of heart/brain (9.843 g/l). The strains

*M. kristinae* and *S. aureus* are cultured in an aerobic medium, and the strain *P. acnes* is cultured in an anaerobic medium, either in the presence of 5 g/l of glucose (traditional carbonaceous source) or in the presence of a product according to the invention (oligosaccharide of degree of polymerisation close to 10 alone, or this oligosaccharide forming a chelate with zinc), or in the presence of the medium alone (control cultures). The quantity of bacteria being cultured is evaluated after 48 hours of culturing by turbidimetry at 750 nm.

Results

The glucose at 5 g/l increases, by a factor of 2.2; 1.6; and 5.2, the quantity of *M. kristinae, S. aureus,* and *P. acne* respectively.

The said oligosaccharide of the degree of polymerisation close to 10, tested at 5.6% (v/v) does not have an effect on the two bacterial strains *M. kristinae* and *S. aureus*. At this concentration, it reduced the quantity of *P. acnes* by 14±2% (number of tests: n=2).

The oligosaccharide-Zn chelate, tested at 5.6% (v/v), increased the *M. kristinae* (non pathogenic strain) by 33%, did not have any effect on *S. aureus,* and inhibited the quantity of *P. acnes* (pathogenic strain) by 74±12%. At 1.6% it still inhibited the strain *P. acnes* by 45±15% (n=2).

Conclusion

In the light of these results, the chelation of zinc significantly increases the inhibitor effect of the oligoalginate of a degree of polymerisation close to 10 on the pathogenic strain *Propionibacterium acnes,* and favours the development of the non-pathogenic strain *Micrococcus kristinae.*

In this way it acquires its beneficial effect in respect of acne.

Detailed below is the additional activity featured by a chelate according to the second example of preparation (oligosaccharide-Mg+Mn Chelate), in addition to the effects referred to above, obtained for a product according to the said first embodiment. Three tests in vitro have established an anti-radical effect for this chelate (the free radicals are the radicals created by the UV radiation which are harmful to the skin).

Superoxide Anion Test

In the first instance, a model of the anti-radical action of an oligosaccharide-Mg+Mn chelate was created by the hypoxanthine/xanthine oxidase system, known for incurring the formation of a highly unstable oxygenated derivative, the superoxide anion ($O_2^-$). This latter generates a sequence of reactions in a cascade effect, which incurs the alteration of the cellular proteins and lipids, as well as of the nucleic acids (DNA). The effects have been compared with those of non-chelated oligosaccharide.

Material and Method

The superoxide anions ($O_2^-$) were created by the addition of xanthine oxidase (55 mUI/ml) to the hypoxanthine (0.85 mM) in a tris-HCl medium, pH=7.4. The superoxide anions were quantified by the formation of formazan (red) based on tetrazolium nitroblue (NBT) at 33 µM, by spectrophotometric dosage under kinetic effect at 560 mm.

The principle of the dosage of the superoxide anions is as follows:

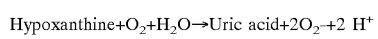
Hypoxanthine+$O_2$+$H_2O$→Uric acid+$2O_2^-$+2 $H^+$ xanthene oxidase

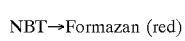
NBT→Formazan (red)

Results

The non-chelated oligosaccharide has an inhibiting effect on the colorimetric reaction which is proportional to its concentration. It exercises an anti-radical activity in respect of the superoxide anion.

The oligosaccharide-Mg+Mn chelate tested at 0.00001; 0.0001; 0.001 and 0.1% (V/V) inhibits the reaction by 12%, 28%, 61%, and 75% respectively.

At 0.33% and 3.3% (V/V), the said chelate inhibits the reaction by 81% and 92% respectively.

Conclusion

The complexing of $Mg^{2+}$ and $Mn^{2+}$ provides the oligoalginate with very powerful anti-radical properties in respect of the superoxide anion.

Test of the Protection of the Cellular Proteins

The anti-radical effect in respect of the superoxide anion led us to test the effects of the oligosaccharide-Mg+Mn complex on fibroblast cultures of human dermis, submitted to a proradical attack provoked by irradiation with UV rays.

Material and Method

Fibroblasts of human dermis are incubated for 24 hours with the chelates of the oligosaccharides-Mg+Mn, at three non-cytotoxic concentrations of 0.04; 0.2; and 1% (v/v). A series of cultures are exposed to UV (0.325 J/cm$^2$), with the other series being kept sheltered from the radiation. The proteins are extracted and their rate of oxidation measured by an immunological dosage. The oxidation of the proteins introduces a carbonyl group at the level of certain amino acids (Lys, Arg, Pro, Thr). The carbonyl groups are transformed into 2,4 dinitrophenyl hydrazone (DNP-hydrazone), and these latter derivatives are quantified by using a specific anti-DNP antibody, followed by a colorimetric reaction.

The results obtained with regard to the protective effect of the said chelates in respect of the oxidation of the said proteins are presented in the table below (by convention, the percentage of protection is considered equal to 100 when the mean quantity is less than or equal to that of the non-irradiated control).

| Sample series | Mean quantity of carbonyl grouping in the proteins ±SEM | Percentage of irradiated control | Protection percentage |
|---|---|---|---|
| Non-irradiated control | 0.46 ± 0.25 | 46 | 100 |
| Irradiated control | 1.11 ± 0.08 | 100 | 0 |
| Treated by chelates at 0.04%, then irradiated | 0.87 ± 0.27 | 78 | 37 |
| Treated by chelates at 0.2%, then irradiated | 0.59 ± 0.05 | 53 | 80 |
| Treated by chelates at 1%, then irradiated | 0.35 ± 0.07 | 31 | 100 |

The UV irradiation increases the oxidation of the proteins by a factor of 2.4. The chelate of the oligosaccharides-Mg+Mn reduces the oxidation of the cellular proteins incurred by the UV radiation, with an effect which follows a dose-effect relationship.

Conclusion

This chelate protects the cellular proteins from proradical attack by UV radiation.

Test of the Protective Effect of Cellular DNA

The protective effects of the DNA were evaluated by measuring the rate of breaking of the DNA in the fibroblasts exposed to UVB radiation.

Material and Method

Fibroblasts of human dermis (drawn from 5 donors) was incubated for 24 hours at 37° C. in the presence of the oligosaccharide-Mg+Mn chelate, or in the presence of a mixture consisting of vitamin C at 50 µg/ml and glutathione at 50 µg/ml, or in the presence of a saline medium (control). A series of cultures was exposed to UVB irradiation (325 mL/cm3), while another series was kept sheltered from irradiation.

These two series were stored at 37° C. for 24 hours. The rate of breaking of the DNA was evaluated by marking the ends of the broken DNA with a nucleotide coupled under fluorescence (the TUNEL method).

This method makes use of the enzyme Terminal Deoxynucleotidyl Transferase (TdT). According to this method, a reduction in the fluorescence of the cells translates into a reduction in the number of breaks in the DNA; i.e. a protective effect.

The results are shown in the table below.

|  | Non-irradiated cells | | Irradiated cells | |
| --- | --- | --- | --- | --- |
|  | $t_0$ | $t_{24}$ | $t_0$ | $t_{24}$ |
| Control without product | +/− | +/− | + | +++ |
| Oligoalginate − Mg + Mn at 0.04% (v/v) | +/− | +/− | + | + |
| Vitamin C at 50 µg/ml + glutathione at 50 µg/ml | +/− | +/− | + | + |
| Control without TdT (negative control) | − | | | |
| Control without TdT (positive control) | >+++ | | | | where
−: no fluorescence
+/−: low intensity
+: medium intensity
+++: high intensity Comments on the Results In the absence of the TdT enzyme, the cells are not fluorescent. In the presence of the enzyme TdT and of an enzyme which degrades the DNA (Dnase 1), a very marked fluorescence is observed. As a result, the specific nature of the marking is established.

In the absence of UVB radiation and in the presence of the enzyme TdT, the cells feature very little fluorescence. After UVB irradiation, and in the presence of the enzyme TdT, the fluorescence of the cells increases.

The cells incubated in the presence of the oligosaccharide-Mg+Mn at 0.04% (v/v) before irradiation, then irradiated, then treated with the enzyme TdT, are less fluorescent.

Conclusion

The oligosaccharide-Mg+Mn protect the dermic fibroblasts from the DNA breaking caused by the UVR rays.

According to a variation in the performance of the first or second method, a product according to the invention consists of a first product, which is obtained in conformity with one of these two methods, and a second product which is obtained on the basis of natural extracts of microscopic algae of the *chlorella* type, according to the following process.

This process consists essentially of carrying out the comminution of the said algae in an alkaline medium, acidifying the extraction substance obtained, eliminating the cellular debris by tangential microfiltration on a filter of which the threshold of retention is 0.22 µm, and concentrating the residual organic elements until a substance is obtained which comprises 5% of active materials, which constitutes the said second product.

The mixing of the said first and second products is carried out in a neutral solvent, such as water, by using concentrations of 5% for each of them.

APPENDIX

I. Determination of the Degree of Mean Polymerisation in Terms of a Number of an Extract of Depolymerised Sodium Alginate by Treatment with Lyase Alginate, by Dosage of Conjugated Double Bonds Lyase alginate is an enzyme which depolymerises the extract of sodium alginate by creating conjugated double binds and semi-acetalic reduction functions.

These conjugated double bonds feature a maximum absorption in the ultraviolet at 235 nm. Their dosage is effected by ultraviolet spectrophotometry, in such a way as to be able to quantify the number of moles of oligo-alginates produced in the volume of the solution.

A given quantity of the reactional medium is taken at different moments of the enzymatic reaction, and the adjustment of the pH is effected of the solution taken, in order to slow down the said reaction. In this embodiment, each drawing of the reactional medium is characterised, on the one hand, by a mass of 10 g and a pH adjusted to 4 with hydrochloric acid if a concentration 1 N.

In addition to this, the said solution taken is diluted in order for its optical density to be below 1.

The optical density (OD) of the said solution is measured for a radiation value of 235 nm, which allows for the dosage of the concentration $C_{bonds}$ (mol. $l^{-1}$) of the conjugated double bonds, thanks to the formula:

$$C_{bonds} = \frac{DO}{\varepsilon} \quad (i)$$

where $\varepsilon$ (5050 l, $mol^{-1}$, $cm^{-1}$) represents the coefficient of molecular extinction of the unsaturated oligo-alginates.

By taking account of the dilutions obtained, it is possible to measure the concentration o conjugated double bonds in the initial reactional medium. In addition, by knowing the concentration by weight of the alginate $C_{alginate}$ in the solution (in g, $l^{-1}$), it is possible to obtain the mean molar weight as a number Mn (g, $mol^{-1}$) of the samples taken, by means of the formula $$M_n = \frac{C_{alginate}}{C_{bonds}} \quad (ii)$$

The mean degree of polymerisation is deduced as a number DPn by means of the following formula:

$$Dp_n = \frac{M_n}{M_0} \quad (ii)$$

where $M_0$ is the molar weight of a constituent unit of the molecule of sodium alginate ($M_0$=216 g, $mol^{-1}$).

II. Determination of Mean Degree of Polymerisation as a Number of an Extract of Depolymerised Sodium Alginate by Means of Hydrolysis in an Acid Medium, by the Method of Sugar Reducer Dosage (Known as the SOMOGYI-NELSON Method)

Acid hydrolysis of the alginate generates a semi-acetalic reduction function and a hydroxyl function. The dosing of the aid reduction function is effected by means of the following solutions:

Solution A
  Anhydrous sodium carbonate: 25 g
  Potassium and sodium tartrate: 25 g
  Sodium hydrogen carbonate: 20 g
  Anhydrous sodium sulphate: 200 g
These four constituents are dissolved in 1 l of ultra pure water Solution B
  Monohydrated copper sulphate: 30 g
  Concentrated sulphuric acid: 4 drops
These substances are dissolved in 200 ml of ultra-pure water.
Solution C
  Obtained by adding 25 parts by volume of solution A to one part by volume of solution B.
Solution D
  Ammoniacal molybdate: 25 g
  Concentrated sulphuric acid: 39 g
  Sodium arseniate: 3 g
These substances are dissolved in 500 ml of ultra-pure water.

The principle of this method resides in the fact that the said semi-acetalic function is oxidised by the copper and creates copper oxide, which reacts with the arseniomolybdic complex in order to produce a molybdate oxide.

The operative method is described below.

1 ml of Solution C is added to 1 ml of the solution to be measured into a test tube, and the mixture obtained is heated for 20 minutes in a water bath. The said mixture is then cooled rapidly by pouring running water over the tube. 1 ml f Solution D and 12 ml of ultra-pure water are then added in succession to the said mixture.

With the molybdate oxide which is produced featuring a maximum absorption for radiation of a wavelength equal to 660 nm, the optical density of the solution obtained at this wavelength is then measured.

Calculations allow for the mean molar mass to be determined as a number, and from this it can be deduced that the mean degrees of polymerisation as numbers of the hydrolysed alginate are the same as those indicated in Paragraph 1.

What is claimed is:

1. A process for making a skin care product, said process comprising the steps of:
   (a) providing a solubilized algae extract containing sodium alginate having linked chains of sodium α-L-guluronate and sodium β-D-mannuronate, and
   (b) enzymatically depolymerizing said solubilized extract responsive to an action of an alginate lyase enzyme in order to cut links between chains of said sodium alginate.

2. The process of claim 1 wherein the algae is *chlorella*.

3. The process of claim 1 and the further step comprising hydrolysing said depolymerized extract in an acid medium in order to obtain a product characterized by a reduced degree of polymerization.

4. A skin care product made by the process of claim 1 wherein said product comprises oligo-alginate chains and uronic acids.

5. A skin care product in accordance with claim 4, further comprising at least one oligo-element in a cationic form, said oligo-element forming a chelate with the oligo-alginate chains.

6. A skin care product in accordance with claim 5 wherein the chelate comprises $Zn^{2+}$ ions.

7. A skin care product in accordance with claim 5, wherein the chelate comprises $Mn^{2+}$ and $Mg^{2+}$ ions.

8. A skin care product in accordance with any one of the claims 4–7 wherein said product comprises, at least natural extracts of algae of the type *chlorella*.

9. A product in accordance with any one of the claims 4–7 wherein said product protects Langerhans' cells of the epidermis against ultraviolet radiation.

10. A product in accordance with any one of the claims 4–7 wherein said product increases an epidermic concentration of interleukin 1α.

11. A product in accordance with any one of the claims 5–7 wherein said product provides an anti-radical effect in respect of free radicals produced by ultraviolet radiation.

12. A product in accordance with claim 11, wherein said product protects cell of the dermis from an oxidation of proteins.

13. A product in accordance with claim 11, wherein said product protects cell of the dermis against a breaking of a DNA.

14. A product in accordance with any one of the claims 5–7 wherein said product inhibits enzyme 5α reductase.

15. A product in accordance with any one of claims 5–7 wherein said product inhibits acne caused by a pathogenic baterial strain Propionibacterium.

* * * * *